(12) United States Patent
Suzuki (10) Patent No.: US 10,981,086 B2
(45) Date of Patent: Apr. 20, 2021

(54) PURIFICATION COLUMN

(71) Applicant: Toray Industries, Inc., Tokyo (JP)

(72) Inventor: Hisashi Suzuki, Otsu (JP)

(73) Assignee: Toray Industries, Inc.

( * ) Notice: Subject to any disclaimer, the term of this patent is extended or adjusted under 35 U.S.C. 154(b) by 0 days.

(21) Appl. No.: 16/478,882

(22) PCT Filed: Dec. 26, 2017

(86) PCT No.: PCT/JP2017/046555
§ 371 (c)(1),
(2) Date: Jul. 18, 2019

(87) PCT Pub. No.: WO2018/139145
PCT Pub. Date: Aug. 2, 2018

(65) Prior Publication Data
US 2019/0381422 A1 Dec. 19, 2019

(30) Foreign Application Priority Data

Jan. 30, 2017 (JP) .............................. JP2017-013902

(51) Int. Cl.
*B01D 15/20* (2006.01)
*B01D 15/22* (2006.01)
(Continued)

(52) U.S. Cl.
CPC ............... *B01D 15/22* (2013.01); *A61M 1/34* (2013.01); *B01D 15/206* (2013.01);
(Continued)

(58) Field of Classification Search
CPC ...... B01D 15/22; B01D 15/206; B01D 63/02; B01D 63/021; B01D 63/022;
(Continued)

(56) References Cited

U.S. PATENT DOCUMENTS 6,659,289 B1 * 12/2003 Masuko .............. A61M 1/3679
210/435
8,236,177 B1    8/2012 Wood
9,802,842 B2   10/2017 Shiki
2011/0033704 A1 *  2/2011 Nakao ................... B01J 20/262
428/398

(Continued)

FOREIGN PATENT DOCUMENTS

JP    59177063 A    10/1984
JP    08294531 A    11/1996

(Continued)

OTHER PUBLICATIONS

International Search Report and Written Opinion for International Application No. PCT/JP2017/046555, dated Feb. 13, 2018—6 pages.

*Primary Examiner* — Benjamin L Lebron
(74) *Attorney, Agent, or Firm* — RatnerPrestia (57) ABSTRACT

The invention provides a purification column that contains an adsorbent and shows excellent adsorptivity. Specifically, this purification column is provided with an adsorbent and a case that contains the adsorbent and has a tubular housing and treatment fluid supply port and discharge port at both ends of the housing. The purification column is characterized in that: a distribution plate is disposed at least on one end face side of the adsorbent; the distribution plate has a plurality of openings that allow communication of the treatment fluid, a support body, and a protrusion extending from the supporting body to the adsorbent side; and at least part of the protrusion is inserted into the adsorbent.

8 Claims, 5 Drawing Sheets

(51) Int. Cl.
    *B01J 20/26*     (2006.01)
    *B01J 20/28*     (2006.01)
    *B01J 20/285*     (2006.01)
    *G01N 30/60*     (2006.01)
    *A61M 1/34*     (2006.01)

(52) U.S. Cl.
    CPC ........... *B01J 20/262* (2013.01); *B01J 20/285* (2013.01); *B01J 20/28016* (2013.01); *B01J 20/28023* (2013.01); *G01N 30/60* (2013.01)

(58) Field of Classification Search
    CPC .............. B01D 63/024; B01D 2313/23; B01D 2321/04; B01D 2321/168; B01D 65/02; A61M 1/34; B01J 20/262; B01J 20/28016; B01J 20/28023; B01J 20/285; G01N 30/60
    See application file for complete search history.

(56) References Cited

U.S. PATENT DOCUMENTS

| | | | |
|---|---|---|---|
| 2013/0306545 A1* | 11/2013 | Shinohara | ............ B01D 63/022 210/321.89 |
| 2015/0197431 A1* | 7/2015 | Shiki | .................... B01D 63/021 210/652 |

FOREIGN PATENT DOCUMENTS

| | | |
|---|---|---|
| JP | 2004261028 A | 9/2004 |
| JP | 2011156022 A | 8/2011 |
| JP | 2011224026 A | 11/2011 |
| JP | 2014210174 A | 11/2014 |
| JP | 2015025377 A | 2/2015 |
| JP | 2015131267 A | 7/2015 |
| JP | 2017186722 A | 10/2017 |

* cited by examiner

PURIFICATION COLUMN

CROSS REFERENCE TO RELATED APPLICATIONS

This is the U.S. National Phase application of PCT/JP2017/046555, filed Dec. 26, 2017, which claims priority to Japanese Patent Application No. 2017-013902, filed Jan. 30, 2017, the disclosure of these applications being incorporated herein by reference in their entireties for all purposes.

FIELD OF THE INVENTION

Our invention relates to a purification column having an adsorbent (adsorption carrier).

BACKGROUND OF THE INVENTION

Purification columns to adsorb substances to be removed from a fluid may have adsorbent of beads, fiber bundle consisting of a plurality of fibers, or knitted fabric. The adsorbent of beads packed uniformly in the purification column is advantageous with less uneven flow of fluid because the fluid has a small difference of channel resistance between an axial direction connecting openings at both housing ends of the purification column and a radial direction orthogonal to the axial direction.

On the other hand, although surface area per unit volume of adsorbent may be increased to improve the purification column in adsorptivity, small diameter of adsorbent beads might narrow gaps between beads to increase pressure loss so that the fluid doesn't flow well. Further, spherical shape of beads leads to disadvantageous small surface area per, unit volume.

The adsorbent of knitted fabric cannot be made porous easily by forming adsorption holes on the fiber and might cause a pressure rise in the purification column when the fluid is viscous.

In contrast to the beads and knitted fabric, the fiber bundle consisting of fibers can be packed in parallel with the axial direction connecting openings at both housing ends of the purification column.

To keep the adsorbent inside the purification column, a filter having many fine holes or a resin layer having through-holes is provided on an end for supplying and/or discharging the fluid from the purification column. The filter or the resin layer has an opening as large as capable of flowing the fluid but the adsorbent.

It is known that a channeling (which means non-uniform flow distribution) might deteriorate the adsorptivity of the purification column. The channeling might generate a region where the fluid doesn't contact the adsorbent or a region where the flow of fluid stagnates, so that the effective surface area of the adsorbent decreases to deteriorate the adsorptivity of the purification column.

The channeling may be caused by non-uniform distribution of adsorbent packed in the purification column, or by small ratio L/D of length L to average diameter D of the packing section of adsorbent.

To prevent the channeling, Patent document 1 discloses a blood purification column capable of flow blood widely in the cross section of channel in the column by adjusting the channel resistance of blood flowing according to the part of the filter to support adsorbent particles in the column.

Patent document 2 discloses a purification column having a housing, in which hollow fibers are contained, of cylindrical casing of which both ends are provided with a partition wall through which a through-hole communicates the outside and the inside.

Patent document 3 discloses a blood treatment device comprising a column provided with inserts inside to block the shortest path from inlet to outlet of blood flowing in the column.

Patent document 4 discloses a blood purification device having a container containing an adsorbent, an elastic body provided on both ends of the adsorbent and a supporting body to support the adsorbent and the elastic body from both ends of the elastic body.

Patent document 5 discloses a hollow fiber membrane module comprising a distribution regulation member provided at an end of the hollow fiber bundle and a rectifier tube surrounding a part of the end of the hollow fiber bundle, the rectifier tube being partially fixed to an adhesive fixing layer, the distribution regulation member being included in the adhesive fixing layer to reduce a non-uniform density distribution of the hollow fiber in the hollow fiber bundle.

PATENT DOCUMENTS

Patent document 1: JP2011-156022-A
Patent document 2: JP2014-210174-A
Patent document 3: JP-H08-294531-A
Patent document 4: JP-S59-177063-A
Patent document 5: JP2015-131267-A

SUMMARY OF THE INVENTION

The above-described technologies have the following problems.

Namely, when the channel resistance of the fluid passing each part of filter is changed, it is difficult that the flow distribution of fluid in the adsorbent is controlled unless the filter firmly contacts the adsorbent, although the flow distribution of fluid just passing through the filter can be controlled. Particularly when the adsorbent is not fixed to the resin layer or the like, the packing distribution of adsorbent in the housing tends to fluctuate according to the handling condition such as storing, conveying and usage of purification column, and therefore the rectification effect of filter might not contribute to the flow distribution of fluid as a whole purification column.

When the channeling resistance at each part of filter is changed to control the flow distribution of the fluid, it is possible that the channel resistance is increased at a part of strong flow of the fluid and is decreased at a part of weak flow of the fluid so that the flow distribution of the fluid in the cross section of channel in the column can be uniform after passing through the filter. However, the opening of the part of filter has to be minimized to increase the channel resistance, and therefore continuous usage might increase pressure at the part.

Further, when the partition walls at both ends of casing are provided with through-holes penetrating the partition wall to communicate the inside and outside of casing, the fluid can flow into only through-hole parts partially provided. The fluid might stay at both ends of partition walls and deteriorate adsorption efficiency because of channeling or the like. From a viewpoint of manufacturing, the cost might be increased by forming partition walls, using resin and losing adsorbent to be buried under the partition wall. Further, the manufacturing process may be complicated for forming partition walls having through-holes.

Furthermore, when the purification column is provided with inserts inside to block the shortest path from inlet to outlet of blood flowing in the purification column, the packing part of adsorbent should be greater for providing the inserts inside the purification column. As a result, the operation of purification column might deteriorate while the volume of fluid flowing in the purification column might be increased. Particularly when the purification column is used for blood purification, increased blood volume increases the extracorporeal circulation volume of blood taken from a patient who may have heavier load to cause an extremely important problem. Further, it is difficult that inserts are provided in the adsorbent of fiber bundle. Even when inserts are provided in the fiber bundle, it is difficult that the fiber bundles are uniformly provided as dispersed in the purification column, so that adsorptivity might deteriorate by the channeling from non-uniform part of fiber bundle.

When supporting bodies are provided at both sides of elastic body to hold the adsorbent and the elastic bodies provided at both ends of the adsorbent, the flow of fluid in the purification column may not be controlled although microparticles generated from the adsorbent can be caught with the elastic body. When the elastic body is pressed by the supporting body, a porous structure provided in the elastic body might deform to increase pressure locally.

When the rectifier cylinder is attached and the distribution regulation member for preventing hollow fibers from being biased is inserted, the biased density distribution of hollow fibers can be reduced. However, the volume of fluid flowing in the purification column might be increased like the above-described case of inserts which blocks the shortest path from inlet to outlet of fluid. From a viewpoint of manufacturing, it is extremely difficult that the biased distribution regulation member is provided in fiber bundles packed densely. Further, the cost might be increased by forming adhesive fixing layer while the manufacturing process might be complicated, like the above-described case of the partition walls which are provided at both ends of casing and are provided with through-holes penetrating the partition wall to communicate the inside and outside of casing.

Accordingly, it could be helpful to provide a purification column containing an adsorbent, wherein the flow distribution of fluid in the purification column is controlled so that the fluid volume in the purification column doesn't increase to suppress the channeling, and wherein the fluid stays at a minimized part to achieve excellent adsorptivity.

To solve the above-described problems, our invention has the following configuration.

A purification column comprising: an adsorbent; a case which contains the adsorbent and has a cylindrical housing, a supply port and a discharge port for a fluid at both ends of the housing; and a distribution plate provided at an end face side of the adsorbent, the distribution plate having: a plurality of openings capable of communicating the fluid; a supporting body; and a salient extending from the supporting body toward the adsorbent, the salient being inserted at least partially into the adsorbent.

Our invention makes it possible to provide a purification column containing an adsorbent, wherein the flow distribution of fluid in the purification column is controlled so that the fluid volume in the purification column doesn't increase to suppress the channeling, and wherein the fluid stays at a minimized part to achieve excellent adsorptivity.

Further, the distribution plate having a plurality of openings capable of communicating the fluid can reduce the stagnation of fluid to improve the adsorption efficiency.

Furthermore, the distribution plate having a salient to be inserted into the adsorbent can control the packing rate of adsorbent according to the position of the salient. Therefore, the diameter of the packing part of adsorbent doesn't have to be increased. Therefore, it would be advantageous for easy handling of purification column without complicated manufacturing process while the volume for fluid inside the purification column can be minimized.

DETAILED DESCRIPTION OF EMBODIMENTS OF THE INVENTION

In the specification, the purification means a process to remove object substance from fluid to be treated by adsorption utilizing characteristics of adsorbent.

For example, when our purification column is used for the purpose of blood purification, the target substance may be cytokine, endotoxin, β2-microglobulin (which may be abbreviated as β2-MG), leukocyte or the like, although it is not limited thereto in particular.

Figure 8:
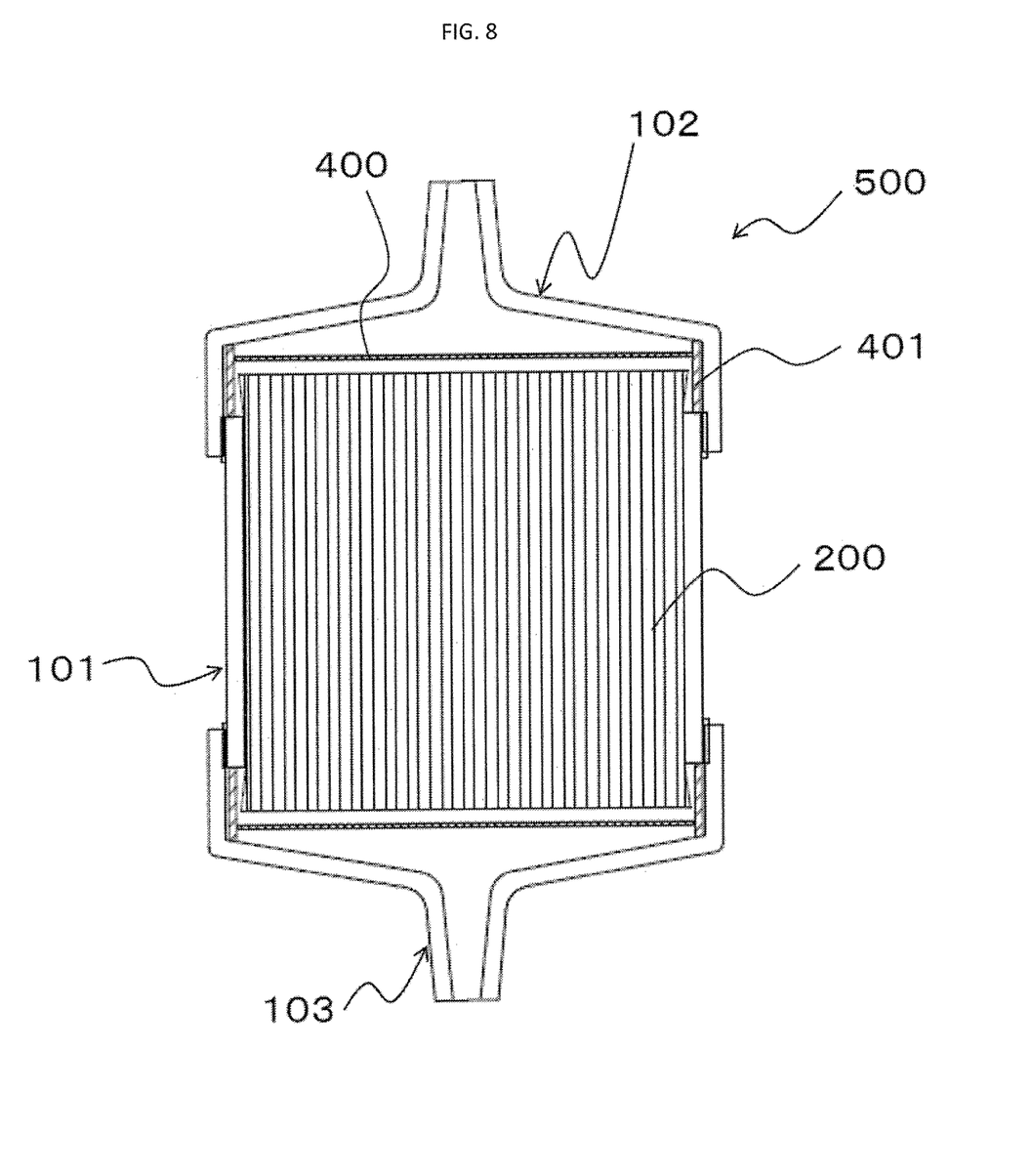
FIG. 8 is a longitudinal cross-section view showing a conventional purification column.

FIG. 8 shows a conventional purification column. As shown, a conventional purification column is provided with filter 400 fixed to filter supporting body among housing 101, supply port 102 and discharge port 103 to hold adsorbent 200 in purification column 500.

Figure 1:
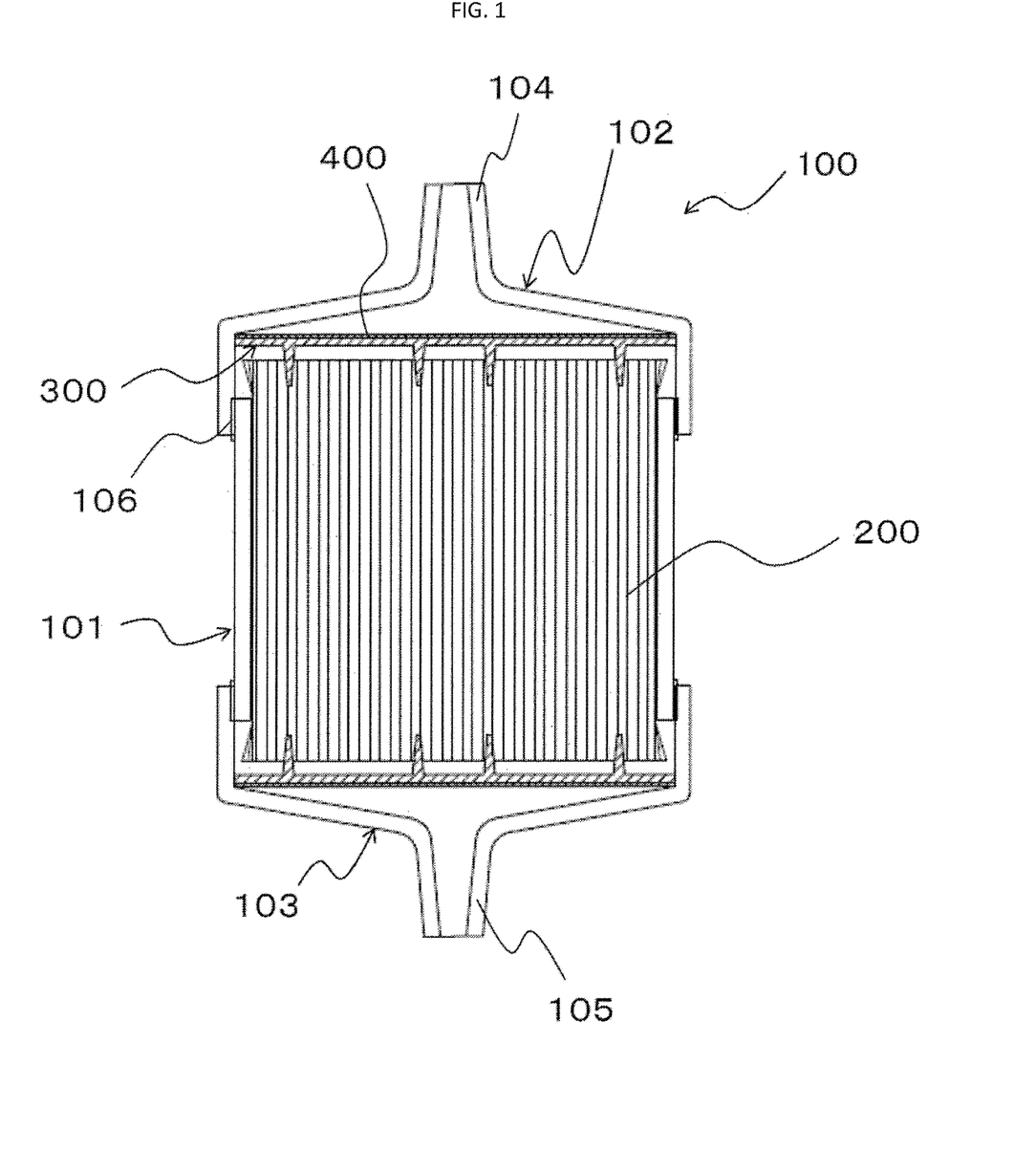
FIG. 1 is a longitudinal cross-section view showing an example of our purification column.

Hereinafter, Examples of our invention will be explained with reference to figures. FIG. 1 shows an example of our purification column, which is not limited to the following examples.

In FIG. 1, purification column 100 comprises cylindrical (or preferably circular cylindrical) housing 101, supply port 102 of fluid provided at the opening end of housing 101 and discharge port 103. Supply port 102 and discharge port 103 are provided with supply nozzle 104 to supply fluid to purification column 100 and discharge nozzle 105 connected to a pipe for discharging the fluid from purification column 100. The nozzles are opened toward the inside of housing 101. It is preferable that the nozzles are disposed as coaxial with the center line along the axial direction connecting openings at both ends of housing 101.

Adsorbent 200 is contained in a case consisting of housing 101, supply port 102 and discharge port 103. When La indicates a packing length of adsorbent 200 in the axial direction of purification column while Lh indicates a length of housing 101, the formula of "La>Lh" is satisfied in this case, although other formula of "La=Lh" or "La<Lh" may be satisfied. The said "axial direction" of purification column 100 means a direction connecting openings at both ends of housing 101 of purification column 100.

It is preferable that adsorbent 200 contained in the case is a bead or a fiber bundle consisting of a plurality of fibers. The fiber bundle is advantageous because the surface area per unit volume of the adsorbent can be increased. Further, when the fiber bundles are disposed along the axial direction of the purification column, channels of fluid can be provided in parallel with fibers constituting the adsorbent to suppress the channel resistance. Furthermore, the adsorbent can be improved in packing density in purification column 100 as described. Accordingly, it is preferable to employ the fiber bundle form.

From viewpoints of easy forming and cost, it is preferable that the adsorbent having a form of fiber or bead is made of organic substance such as polymethylmethacrylate (abbreviated as PMMA), polyacrylonitrile (abbreviated as PMMA PAN), polysulfone, polyether sulfone, polyaryl ether sulfone, polypropylene, polystylene, polycarbonate, cellulose, cellulose triacetate and ethylene-vinyl alcohol copolymer. When the fluid of blood is treated, it is preferable that the adsorbent is made of polysulfone, PMMA, PAN, cellulose or the like capable of adsorbing proteins.

The fiber may be a hollow fiber or a solid fiber. It is preferable to employ the solid fiber. The said "hollow fiber" means a cylindrical fiber form. The said "solid fiber" means a fiber form other than the cylindrical fiber form of the "hollow fiber". The hollow fiber might deteriorate adsorption efficiency of purification column when there is a difference of pressure loss of fluid between the inside and outside of the hollow fiber so that the flow rates of fluid flowing inside and outside the hollow fiber are different. Therefore some measures are required to prevent the hollow fiber from causing the problem.

The fiber having too small a fiber diameter (corresponding to inside/outside diameter for hollow/solid fiber) might increase the pressure loss of purification column or might pass through filter 400. Further, the fiber might decrease physical strength to cause fiber breakage or microparticle generation at the time of assembly or use of purification column.

On the other hand, the fiber having too large a fiber diameter might deteriorate adsorptivity of purification column because surface area per unit volume is decreased to decrease the contact area to the fluid.

Accordingly, it is preferable that the fiber has a fiber diameter of 1,000 μm or less. It is more preferably 400 μm or less and is further preferably 190 μm or less. It is preferable that the lower limit is 10 μm. It is more preferably 20 μm and is further preferably 50 μm.

The fiber diameter of fiber can be measured with a projector (V-10A made by Nikon Corporation, or the like) by a method in which 50 pieces of randomly selected fibers contained in the case are washed with pure water and sandwiched between a slide glass and a cover glass. The outside diameter (which means outermost diameter) of fiber having a circular cross section or the equivalent circle diameter of outermost periphery of fiber having a shape other than the circle is determined by averaging values measured for randomly selected each two parts of a fiber as rounding it off to the closest whole number.

The above-described fiber bundle is unidirectionally oriented with the fibers which may have the same specification or different specifications. To control the packing rate of adsorbent and prevent the adsorptivity from lacking, it is preferable that the number of yarns is 0.100 or more, and is preferably 500 or more. Although there is no specific upper limit, it is preferably 1,000,000 or more because too many yarns might deteriorate productivity of purification column.

The bead may have a shape of polyhedron such as cube, ellipse or sphere. It is preferably a sphere from a viewpoint of easy production. It is possible that the beads have a uniform particle diameter of all the same, or alternatively have a distribution of particle diameter with different particle diameters. The beads having a uniform particle diameter have an average particle diameter equal to the particle diameter of each bead. On the other hand, the beads having a distribution of particle diameter have an average particle diameter calculated from diameters of individual beads. Specifically, the average particle diameter can be calculated by dividing a summation of individual bead particle diameters $d_i$ by number N of measured samples.

The individual bead particle diameters can be determined by measuring enlarged particle diameters on an image observed with an optical microscope to calculate actual particle diameters by dividing the enlarged particle diameters by the magnification ratio. The average particle diameter can also be determined with a commercially available device for measuring particle diameter of powder or the like. For example, a Coulter counter (made by Beckman Coulter, Inc.) utilizing the change of electric resistance in a water solution can be used to determine the average particle diameter according to a preliminarily obtained conversion factor of relation between the measured value of the bead and the actual particle diameter.

The beads having too small an average particle diameter might have a smaller gap between beads to increase the channel resistance, so that the pressure loss of purification column is increased. On the other hand, the beads having too large an average particle diameter might decrease the contact area between beads and fluid to deteriorate adsorptivity. Accordingly, it is preferable that the beads have an average particle diameter of 80 μm or more, preferably 150 μm or more. It is preferable that the upper limit is 500 μm, preferably 300 μm.

Although the beads may not have a uniform distribution of particle diameter, too broad distribution of particle diameter might allow many small beads exist under the same average particle diameter. As a result, the fluid might have a biased flow in the purification column because the fluid cannot easily pass through small gaps formed between beads.

Distribution plate 300 is provided on at least one end face side of adsorbent 200. The said "one end face side" means a direction of one end of adsorbent 200 with respect to the axial direction of purification column 100. In FIG. 1, distribution plates 300 are provided between open end of housing 101 and supply port 102 as well as between open end of housing 101 and discharge port 103 respectively, although the plate may be provided on only one end face of adsorbent 200. In FIG. 1, a space is provided between distribution plate 300 and adsorbent 200, although the plate may firmly contact the adsorbent.

At least one part of salient 303 of distribution plate 300 is inserted in adsorbent 200. When adsorbent 200 is a fiber bundle consisting of a plurality of fibers, the said "inserted" means a state that salient 303 comes in a gap between fibers. When adsorbent 200 consists of several beads, the said "inserted" means a state that salient 303 comes in a gap between beads. Namely, it chiefly means a state that salient 303 of distribution plate 300 is inserted in a gap between individual components although there may be a part of intrusion inside as destroying components of adsorbent 200.

Filter 400 is provided between supply port 102 or discharge port 103 and distribution plate 300 to cover opening 302 of distribution plate 300. Filter 400 has many openings having a size through which the fluid passes and adsorbent 200 cannot pass. With such a configuration, adsorbent 200 contained in purification column 100 is held so that adsorbent 200 does not flow out of purification column 100 along with the flow of fluid.

From viewpoints of formability, strength and operability, shapes and materials of housing 101, supply port 102 and discharge port 103 can be selected appropriately. It is possible that housing 101 has circular cylindrical form, ellipse cylindrical form or prismatic cylindrical form. The shapes of supply port 102 and discharge port 103 can be selected appropriately according to the shape of housing 101. From viewpoints of productivity and disposability, it is preferable that they are made of a metal or a resin such as polypropylene, polycarbonate, polystyrene, polyvinyl chloride and acrylonitrile-butadiene-styrene (ABS).

Joints 106 between housing 101 and supply port 102 or discharge port 103 are, designed appropriately, from viewpoints of prevention of leakage from joint 106 and the joint strength. They may be jointed by screw, adhesive, fusion or combination thereof. An elastic sealing member such as O-ling may be provided between housing 101 and supply port 102 or discharge port 103.

Filter 400 may be made of a metal or a resin such as polyester, polyethylene, polypropylene and nylon, although it is not limited there to in particular. Filter 400 may be formed integrally with distribution plate 300 by forming a whole shape with the same material at a time. Alternatively, filter 400 may be prepared separately from distribution plate 300 in a process and then be integrated with distribution plate 300 through another process. Alternatively, the filter may be integrated with filter supporting body 401 other than distribution plate 300. Besides, filter 400 as a member separate from distribution plate 300 should be provided between distribution plate 300 and supply port 102 or discharge port 103. When I do not establish distribution plate 300, I locate filter 400 between adsorbent 200 and supply port 102 and/or discharge port 103.

Hereinafter, the flow of the fluid will be explained with reference to FIG. 1. The fluid supplied to purification column 100 through supply nozzle 104 flows in adsorbent 200 through a space inside supply port 102, filter 400 and opening 302 of distribution plate 300. The fluid contacts adsorbent 200 as flowing toward the discharge side through gaps of adsorbent 200, opening 302 of distribution plate 300 and filter 400. The fluid passing through filter 400 flows out through discharge nozzle 105 from a space inside discharge port 103. In FIG. 1, supply port 102 is provided at the upper side of purification column 100, although it is possible that supply port 102 is provided at the lower side while discharge port 103 is provided at the upper side so that the fluid flows upward in purification column 100.

In detail, the fluid flowing through supply nozzle 104 tends to generate a strong flow right under the supply nozzle by the inertia at the time of the inflow while the strength of flow tends to decrease with distance from supply nozzle 104 in the radial direction of purification column 100. Accordingly, adsorbent 200 has a velocity distribution in the channel cross section, in which the velocity at a part facing the supply nozzle tends to be fast and the velocity at another part distant from the part tends to be slower.

To eliminate such a tendency, salient 303 of distribution plate of purification column 100 is inserted to the adsorbent to control the packing rate at adsorbent end face 201 so that the channel resistance of fluid flowing in adsorbent 200 is greater at a part facing the nozzle and is smaller at another part with distance from the part. With such a configuration, the fluid flowing in a space inside supply port 102 can also flow to parts with distance from the part facing the supply nozzle to improve non-uniform velocity distribution in adsorbent 200.

Figure 6:
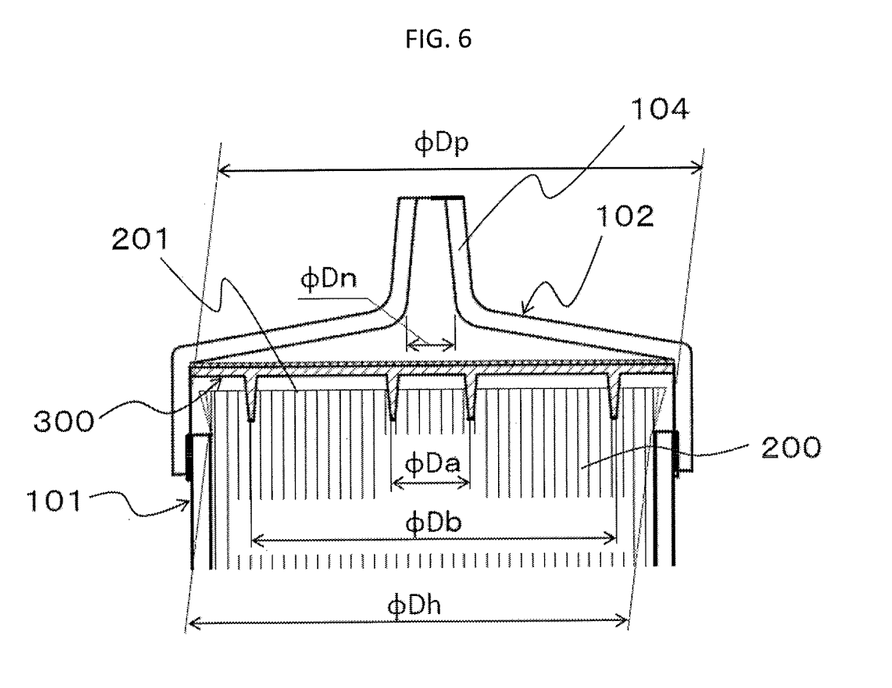
FIG. 6 is a partial longitudinal cross-section view showing a part around an end of adsorbent container of our purification column provided with a distribution plate shown in FIG. 2.

The said "packing rate" can be calculated by dividing any cross-section area of adsorbent 200 by the cross-section area in the case in the same cross section, the cross section of adsorbent 200 is orthogonal to the axial direction of purification column 100 in the section containing adsorbent 200. FIG. 6 is a partial longitudinal cross-section view showing a part around an end of adsorbent container of our purification column. The packing rate will be explained with reference to the figure. When the contribution of distribution plate 300 is disregarded, the packing rate at adsorbent end face 201 is expressed by the formula of "Aa/0.25πΦDp$^2$× 100", where ΦDh indicates an inside diameter of end of housing 101, ΦDp indicates an inside diameter of supply port corresponding to the height of adsorbent end face 201, and Aa indicates a cross-section area of adsorbent 200 in the cross section orthogonal to the axial direction of purification column 100. Similarly, the packing rate at end of housing 101 (including a case that adsorbent end face 201 is provided at end of housing 101) is expressed as the formula of "Aa/0.25π Dh$^2$×100".

The said "channel resistance" means a resistance of fluid passing through a region of unit area of adsorbent.

Even the flow toward discharge nozzle 105 from the inside of adsorbent 200 through distribution plate 300 at the discharge side tends to generate a strong flow at a part facing discharge nozzle 105 while the strength of flow tends to decrease with distance from discharge nozzle 105 in the radial direction. To eliminate such a tendency, salient 303 of distribution plate can be inserted to adsorbent 200 to control the packing rate at adsorbent end face 201 so that the channel resistance of fluid flowing from adsorbent 200 is greater at a part facing the nozzle and is smaller at another part with distance from the part to improve the non-uniform velocity distribution.

The non-uniform velocity distribution of fluid in adsorbent 200 may be derived from a distribution of adsorbent 200 contained in housing 101. When the distribution of adsorbent 200 contained in housing 101 generates sparse or dense part, the channel resistance becomes higher to prevent the fluid from flowing at the dense part and becomes lower to allow the fluid to flow easily at the sparse part. When salient 303 of distribution plate 300 is inserted to adsorbent 200, the distribution of adsorbent 200 in housing 101 can be controlled to prevent non-uniform velocity distribution.

Desirable examples of distribution plate 300 to achieve the above-described object will be explained in detail based on FIG. 2 to FIG. 5. Besides our invention is not limited to the following examples in particular. It is preferable that the distribution plate is made of resin from viewpoints of productivity, compatibility with the case and disposability, although it is not limited thereto in particular. It is preferable to employ polypropylene, polycarbonate, polystyrene, polyvinyl chloride, acrylonitrile-butadiene-styrene (ABS) although it may be made of a metal.

Figure 2:
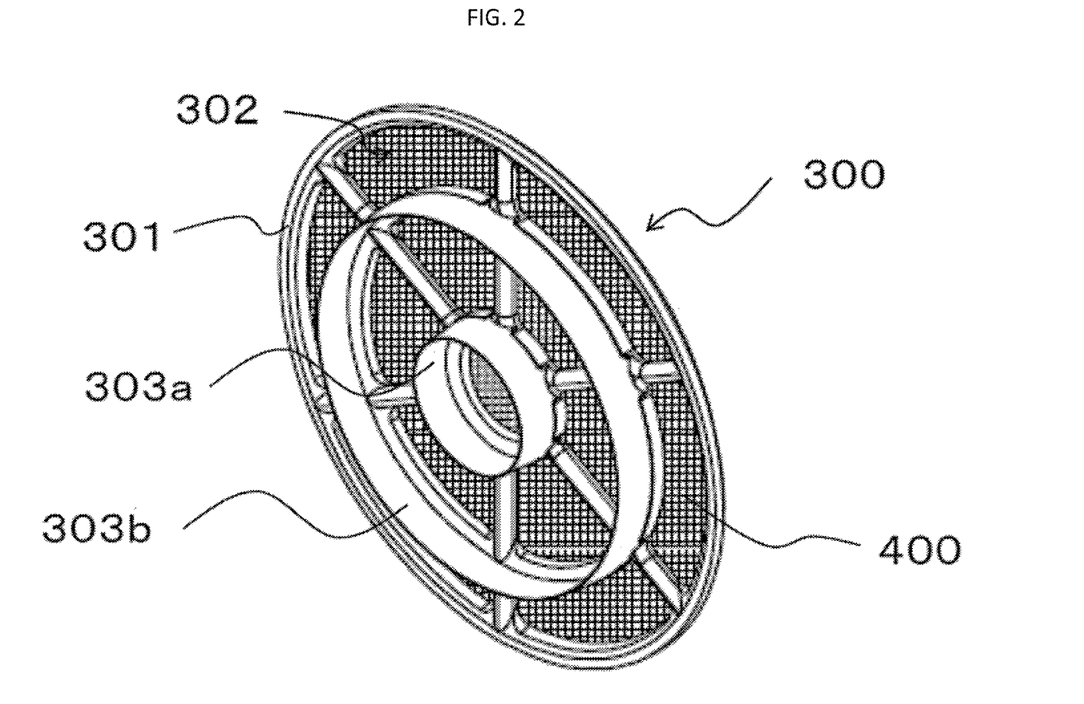
FIG. 2 is an external view showing an example of distribution plate used in our purification column.

FIG. 2 shows an example of distribution plate 300, comprising supporting body 301 consisting of rings and linear ribs disposed radially, openings 302 provided between supporting members through which the fluid can communicate, ring-shaped salients 303a and 303b which is extended from a part of supporting member 301 and disposed as coaxial with the central axis of housing 101, and filter 400 integrated with supporting bodies 301 to cover opening 302.

The said "fluid can communicate" means that the pressure loss of fluid passing through opening 302 is much smaller than the pressure loss of fluid flowing in purification column 100 as a whole. That means a channel having a channel resistance smaller than the channel resistance of fluid passing through a region per unit area of filter 400 provided in purification column 100.

Figure 4:
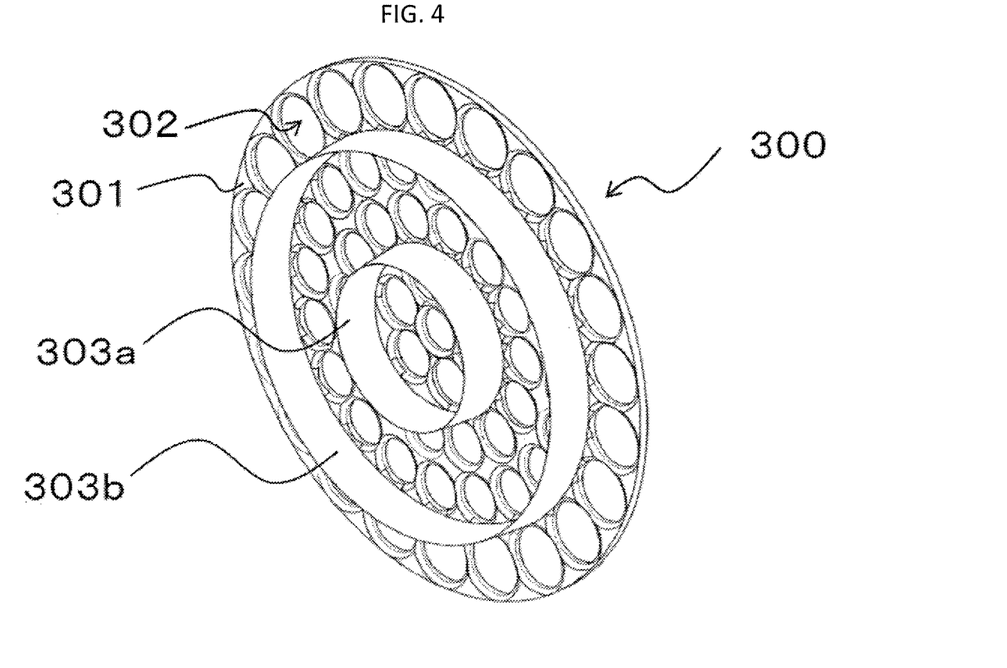
FIG. 4 is an external view showing another example of distribution plate used in our purification column.

Supporting body 301 is configured as capable of communicating fluid regardless of shape or layout of openings 302. It is possible that circular openings 302 are disposed as shown in FIG. 4. It is preferable that openings 302 are uniformly disposed over distribution plate 300 in case that fluid flowing in a space inside supply port 102 generates stagnation or non-uniform flow.

Figure 3:
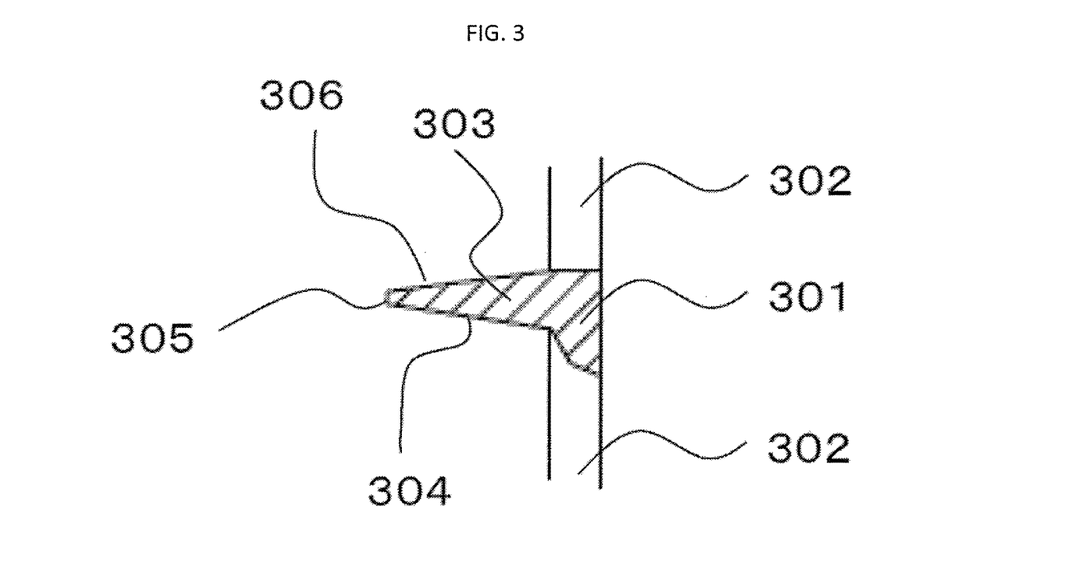
FIG. 3 is a partial cross-section view showing a part around a salient of the distribution plate shown in FIG. 2.

FIG. 3 is a partial cross-section view showing a part around a salient of the distribution plate shown in FIG. 2, where the lower side in FIG. 3 corresponds to the center of distribution plate 300 while the upper side corresponds to the outer peripheral direction. As shown, salient 303 is provided with salient inner periphery 304, salient tip 305 and salient outer periphery 306. From a viewpoint of smooth insertion, it is preferable that salient tip 305 has a narrow width of 0 to 10 mm. It is more preferably 0 to 5 mm and is further preferably 0 to 1 mm.

The length along the axial direction connecting openings at both ends is appropriately designed. The insertion length of salient 303 to adsorbent 200 may be longer so that the flow of fluid flowing in from adsorbent end face 201 is maintained inside the adsorbent while the distribution of adsorbent 200 is approximately fixed. On the other hand, it may be shorter from viewpoints of productivity of distribution plate 300 and smooth insertion to adsorbent 200. Accordingly, it is preferable that the insertion length of salient 303 to adsorbent 200 is 3 to 50% of packing length La of adsorbent 200. It is more preferably 5 to 20%. When a plurality of salients are provided, each insertion length can be set individually.

At least any one face of salient inner periphery 304 and salient outer periphery has an inclination to be tapered from supporting body 301 toward salient tip 305. With such an inclination, salient 303 can be inserted to adsorbent 200 to compress a space surrounded by salient 303 and increase the packing rate at adsorbent end face 201.

Accordingly, the packing rate can be controlled arbitrarily at adsorbent end face 201 by combination of insertion length and inclination provided for salient inner periphery 304 and/or salient outer periphery 306.

From a viewpoint of smooth insertion of salient 303 to adsorbent 200, it is preferable that the inclination angle of the salient from the vertical axial direction (0°) of purification column 100 is 60° or less. It is more preferably 30° or less and is further preferably 10° or less. The salient can be provided with the inclination including a plurality of angles such as 0° (vertical direction) other than a linear inclination.

In FIG. 2, distribution plate 300 has double ring-shaped salients of salient 303a and salient 303b from the center, although it is possible to design a single salient or multiple salients of more than double according to necessity to control the packing rate. The central region in the specification means a region surrounded by salient 303a as the salient closest to the center of distribution plate 300.

Figure 7:
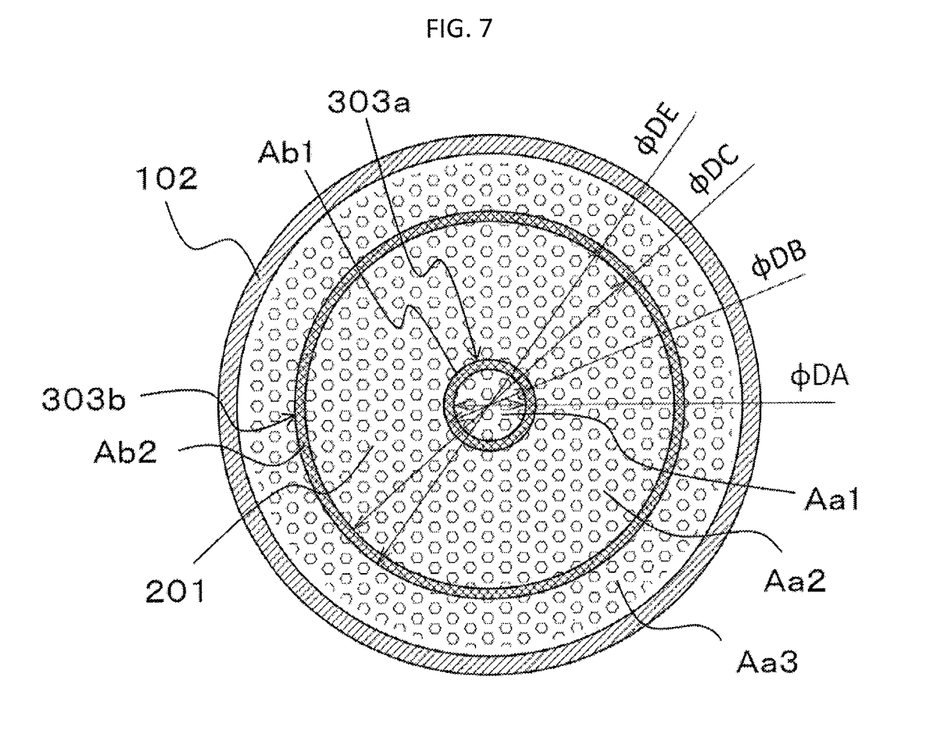
FIG. 7 is a cross-section view showing the purification column shown in FIG. 6, viewed orthogonally to an axis of an end face of fiber bundle.

With reference to FIGS. 6 and 7, the packing rate distribution at adsorbent end face 201 for distribution plate 300 inserted in adsorbent 200 and layout of salients 303 accompanied therewith will be explained. FIG. 7 is a cross-section view showing the purification column shown in FIG. 6, viewed orthogonally to an axis of an adsorbent end face 201. The following explanation about supply port 102 side can be applicable to discharge port 103 side as well.

In FIG. 7, symbol Aa1 indicates an adsorbent cross-section area at adsorbent end face 201 surrounded by salient 303a, symbol Aa2 indicates an adsorbent cross-section area between salients 303b and 303a, and symbol Aa3 indicates an adsorbent cross-section area between supply port 102 and salient 303b. Adsorbent cross-section area Aa as a whole adsorbent cross-section area 201 can be expressed as the formula of "Aa=Aa1+Aa2+Aa3". The average packing rate at adsorbent end face 201 calculated with inserted salient 303 can be expressed as the formula of "(Aa+Ab1+Ab2)/ $0.257\pi\Phi Dp^2 \times 100$", where Ab1 indicates a cross-section area of salient 303a at adsorbent end face 201 while Ab2 indicates a cross-section area of salient 303b. Accordingly, the packing rate at adsorbent end face can be expressed as Formula (I), in which the term of cross-section area of salient 303 contributes increased packing rate at adsorbent end face 201.

Packing rate[%]=(Cross-section area of adsorbent at end face+Cross-section area of salient at end face of adsorbent)/(Inner cross-section area of case at end face of adsorbent)×100    (I)

Next, the packing rate distribution of each region at adsorbent end face 201 sectioned by salient 303 will be explained. Here, $\Phi DA$ indicates an inner periphery diameter of salient 303a at adsorbent end face 201 while $\Phi DB$ indicates an outer periphery diameter thereof. $\Phi DC$ indicates an inner periphery diameter of salient 303b while $\Phi DE$ indicates an outer periphery diameter thereof. $\Phi Da$ indicates a tip diameter based on middle point (corresponding to the tip of salient at the width of 0 mm) of width of salient tip 305 of salient 303a while $\Phi Db$ indicates a tip diameter of salient 303b as well.

As to the central region surrounded by salient 303a, adsorbent cross-section area Aa1 exists in the circular cross-section area having diameter $\Phi Da$ before salient 303 is inserted in adsorbent 200. After salient 303 is inserted, the space is compressed by the inclination provided at salient inner periphery to decrease the diameter from $\Phi Da$ to $\Phi DA$ as keeping adsorbent cross-section area Aa1 constant, so that the packing rate of the center region is expressed as the formula "$Aa1/0.25\pi\Phi DA^2 \times 100$". According to the result of similar thinking thereof, the packing rate of the region between salient 303b and salient 303a can be expressed as the formula of "$Aa2/0.25\pi\Phi DB^2 - \Phi DA^2) \times 100$" while the packing rate of the region between supply port 102 and salient 303b can be expressed as the formula of "$Aa3/0.25\pi(\Phi Dp^2 - \Phi DB^2) \times 100$".

When salient 303 is inserted in the fiber bundle of adsorbent, it is preferable that the packing rate of each region at adsorbent end face (fiber bundle end face) is 40% or more, so that the restraint of adsorbent 200 increases at salient 303 to easily control the packing rate distribution in each region. It is more preferably 50% or more. On the other hand, from viewpoints of deteriorated insertion of adsorbent 200 into salient 303 and risks such as pressure loss increase derived from increased channel resistance, it is preferable that the packing rate with inserted salient 303 at adsorbent end face 201 is 80% or less. It is more preferably 70% or less. Accordingly, when salient 303 is inserted, it is preferable that the packing rate at adsorbent end face 201 expressed as Formula (I) is 40% to 80%. It is more preferably 50% or more, or 70% or less.

From a viewpoint of uniform flow distribution, it is preferable that the central region has the highest packing rate and a channel resistance increased, because the flow of fluid is the strongest at the central region as a part facing supply nozzle 104 and discharge nozzle 105 as described above. Further, it is preferable that ΦDA indicating an inner periphery diameter of salient 303a is 50 to 500% relatively to ΦDn indicating a diameter of lower part of nozzle below supply nozzle 104. It is more preferably 100 to 400%.

Figure 5:
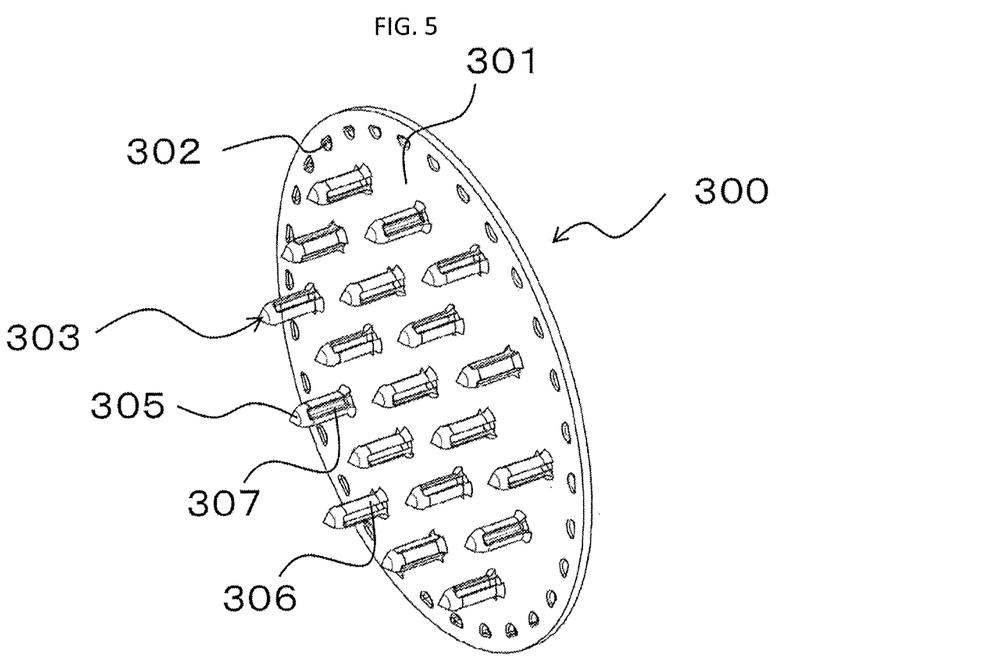
FIG. 5 is an external view showing yet another example of distribution plate used in our purification column.

FIG. 5 shows yet another example of distribution plate, although our invention is not limited thereto in particular. In FIG. 5, a plurality of approximately columnar salients 303 is extended from disk-like supporting body 301. To improve the insertion into adsorbent 200, it is preferable that salient tip 305 has a shape of cone. Inside salient 303, channels are formed as leading from supporting body 301 to salient 303 while the channels lead to salient openings 307 provided on salient outer periphery 306, so that the fluid can communicate to each other.

It is preferable that equally spaced two or more salient openings 307 are provided on salient outer periphery 306 so that the fluid passing through the inside of salient 303 is effectively dispersed around salient 303 of distribution plate 300 installed at the supply side of the fluid, or alternatively, so that the fluid flowing to salient 303 of distribution plate 300 installed at the discharge side of the fluid is effectively collected. In this case, salient openings 307 are provided on salient outer periphery 306 only, although it may be provided on salient tip 305. As well as salient openings 307 provided on salient 303, openings 302 are provided directly on supporting body 301 to prevent the fluid from being retained in this case.

The number and the layout of salients 303 can be designed appropriately, in view of supply of fluid to adsorbent 200 as well as discharge of fluid from adsorbent 200. It is possible to provide salients in each region sectioned to have each divided area of cross section orthogonal to the axis of adsorbent 200. Alternatively, salients may be provided as being disposed radially from the center of distribution plate 300.

From viewpoints of approximate fixation of distribution of adsorbent 200 and maintenance of the flow of fluid flowing from adsorbent end face 201 and salient openings 307 into adsorbent 200 like the above-described case explained with reference to FIG. 2, the insertion length of salient 303 to adsorbent 200 may be longer although the length along the axial direction connecting openings at both ends of the housing is appropriately designed. On the other hand, it may be shorter from viewpoints of productivity of distribution plate 300 and assembly and smooth insertion to adsorbent 200. Accordingly, it is preferable that the insertion length of salient 303 to adsorbent 200 is 3 to 50% of packing length La of adsorbent 200. It is more preferably 5 to 20%. When a plurality of salients are provided, each insertion length can be set individually.

The average packing rate at adsorbent end face 201 calculated with inserted salient 303 can be expressed as the formula of "$(Aa+Ab)/0.25\pi\Phi Dh^2 \times 100$" when adsorbent end face 201 overlaps the end of housing 101, where Ab indicates a total cross-section area of salients 303 calculated in view of the shape of salient outer periphery 306 at adsorbent end face 201. The area increased by salients 303 increases the packing rate at adsorbent end face 201.

When salient 303 is inserted, it is preferable that the packing rate at adsorbent end face 201 is 40% or more, so that the restraint of adsorbent 200 increases at salient 303 to uniformly disperse adsorbent 200 easily inside the case. It is more preferably 50% or more. On the other hand, from viewpoints of deteriorated insertion of adsorbent 200 into salient 303 and risks such as pressure loss increase derived from increased channel resistance, it is preferable that the packing rate at adsorbent end face 201 is 80% or less. It is more preferably 70% or less. Accordingly, when salient 303 is inserted, it is preferable that the packing rate at adsorbent end face 201 expressed as Formula (I) is 40% to 80%. It is more preferably 50% or more, or 70% or less.

EXAMPLES

Example 1

Polymethylmethacrylic resin (PMMA) was spun to prepare solid fibers for adsorbent made of PMMA having a fiber diameter of approximately 109 μm (which was determined with V-10A made by Nikon Corporation) according to a well-known method disclosed in JP2017-186722-A (paragraph 0090). The solid fibers of 210,000 pieces were bundled to prepare a fiber bundle to be contained in a housing. The fiber bundle, of which length was 56.5 mm, protruded by each 5 mm from both ends of the housing of which length was 46.5 mm. The end of housing had inner diameter of 65.8 mm.

Next, a distribution plate of the same type as shown in FIG. 2 with double ring-shaped salients was provided at the fiber bundle end face of the fluid supply side only. The insertion lengths to the fiber bundle of the first salient at the center and the second salient at the outer periphery side were both 5 mm. The widths of salient tips were 0.2 mm. The first salient had tip diameter of 14.3 mm, inner periphery side diameter of 12.8 mm and outer periphery side diameter of 15.4 mm. The second salient had tip diameter of 45.8 mm, inner periphery side diameter of 43.5 mm and outer periphery side diameter of 47.1 mm.

Then, a supply port was attached to the end face of housing at the fluid supply side. The supply nozzle lower diameter of the supply port was 4.4 mm. A fluid measuring jig having a sectioned cross-section area of the same as the area sectioned by the first salient and the second salient of distribution plate provided at the supply side was provided at the housing end face of the fluid discharge side.

In this configuration, the fiber bundle had packing rate of 55.9% at end faces of both the fluid supply side and fluid discharge side before inserting the distribution plate. The end face of fluid supply side of fiber bundle had packing rate of 69.8% in the central region surrounded by the first salient after inserting the distribution plate. It was 63.9% in the region between the first salient and the second salient and was 58.9% in the other region between the supply port and the second salient as well.

Next, the inside of column was washed with water to measure the flow distribution of fluid in each section according to the following method. Table 1 shows the results.

(1) Measurement Method of Flow Distribution of Fluid

The flow distribution was measured according to the following processes to evaluate how the flow distribution was controlled in our purification column.

Water around 20° C. was supplied by a pump at 200 mL/min through the supply port to the purification column, and then the water discharged from the fluid measuring jig provided at the end face of the discharge side was collected with a beaker for 2 minutes. The water flowing in each section of the fluid measuring jig was collected into a beaker provided for each section through a tube connecting the fluid measuring jig and the beaker. Besides, the tube outlet had the same height as that of fiber bundle end face at the discharge side to eliminate the pressure difference between discharge pressure of water from the fiber bundle and discharge pressure of water from the tube so that the flow distribution was not affected by the pressure difference.

The weight of beaker including the collected water was measured with an electronic balance, from which the weight of beaker itself measured in advance was subtracted to determine a measured distributed water weight of each section.

Then, the theoretical ratio of distributed water weight was calculated with Formula (II). The theoretical ratio of 100% means that the water actually flows in the section at the theoretical flow rate. The theoretical ratio of 50% means that the water actually flows in the section at half of the theoretical flow rate while the theoretical ratio of 200% means that the water actually flows in the section at twice the theoretical flow rate. Accordingly, the flow distribution is regarded as being uniform when the theoretical ratio of each section is close to 100%.

(Measured distributed water weight)/(Theoretical distributed water weight calculated from cross-section area of each section)×100[%]  (II)

Example 2

Solid fibers in the same production lot of Example 1 were contained in a housing in the same condition of Example 1.

Similarly to Example 1, a distribution plate of the same type as shown in FIG. 2 with double ring-shaped salients was provided at the fiber bundle end face of the fluid supply side only. The widths of salient tips, the tip diameters of the salients, the inner periphery side diameter and the outer periphery side diameter were the same as Example 1, but the insertion lengths to the fiber bundle of the first salient at the center and the second salient at the outer periphery side were both 10 mm.

Then, a supply port having the same shape as shown in Example 1 was attached to the end face of housing at the fluid supply side. A fluid measuring jig having the same shape as shown in Example 1 was provided at the housing end face of the fluid discharge side.

The fiber bundle had packing rate of 55.9% like Example 1 at end faces of both the fluid supply side and fluid discharge side before inserting the distribution plate in this configuration. Like Example 1, the end face of fluid supply side of fiber bundle had packing rate of 69.8% in the central region surrounded by the first salient after inserting the distribution plate while it was 63.9% in the region between the first salient and the second salient and was 58.9% in the other region between the supply port and the second salient.

Next, the inside of column was washed with water to measure the flow distribution of fluid. Table 1 shows the results.

Example 3

Solid fibers obtained in the same production lot of Example 1 were contained in a housing in the same condition of Example 1.

Next, a distribution plate of the same type as shown in FIG. 2 with double ring-shaped salients was provided at the fiber bundle end face of the fluid discharge side only. The insertion lengths to the fiber bundle of the first salient at the center and the second salient at the outer periphery side were both 4 mm. The widths of salient tips were 0.2 mm. The first salient had tip diameter of 14.3 mm, inner periphery side diameter of 13.6 mm and outer periphery side diameter of 15.4 mm. The second salient had tip diameter of 45.7 mm, inner periphery side diameter of 45.3 mm and outer periphery side diameter of 47.1 mm.

Then, a supply port having the same shape as shown in Example 1 was attached to the end face of housing at the fluid supply side. A fluid measuring jig having a sectioned cross-section area of the same as the area sectioned by the first salient and the second salient of distribution plate provided at the discharge side was provided at the housing end face of the fluid discharge side.

In this configuration, the fiber bundle had packing rate of 55.9% like Example 1 at end faces of both the fluid supply side and fluid discharge side before inserting the distribution plate. The end face of fluid discharge side of fiber bundle had packing rate of 60.4% in the central region surrounded by the first salient after inserting the distribution plate. It was 57.6% in the region between the first salient and the second salient and was 58.6% in the other region between the supply port and the second salient as well.

Next, the inside of column was washed with water to measure the flow distribution of fluid. Table 1 shows the results.

Example 4

Solid fibers obtained in the same production lot of Example 1 were contained in a housing in the same condition of Example 1.

Next, distribution plates of the same type as shown in FIG. 2 with double ring-shaped salients were provided at both end faces of the fiber bundle. The distribution plate provided at the fluid bundle supply side had the same shape of the distribution plate shown in Example 2 while the distribution plate provided at the fluid bundle discharge side had the same shape of the distribution plate shown in Example 34.

Then, a supply port having the same shape as shown in Example 1 was attached to the end face of housing at the fluid supply side. A fluid measuring jig having the same shape as shown in Example 3 was provided at the housing end face of the fluid discharge side.

The fiber bundle had packing rate of 55.9% like Example 1 at both end faces before inserting the distribution plate in this configuration. Like Example 1, the end face of fluid supply side of fiber bundle had packing rate of 69.8% in the central region surrounded by the first salient after inserting the distribution plate while it was 63.9% in the region between the first salient and the second salient and was 58.9% in the other region between the supply port and the second salient. Like Example 3, the end face of fluid discharge side of fiber bundle had packing rate of 60.4% in the central region surrounded by the first salient after inserting the distribution plate while it was 57.6% in the region between the first salient and the second salient and was 58.6% in the other region between the supply port and the second salient.

Next, the inside of column was washed with water to measure the flow distribution of fluid. Table 1 shows the results.

Example 5

Solid fibers obtained in the same production lot of Example 1 were contained in a housing in the same condition of Example 1.

Next, distribution plates of the same type as shown in FIG. 2 with double ring-shaped salients were provided at both end faces of the fiber bundle. The distribution plates provided at both end faces of the fiber bundle had the same shape of the distribution plate shown in Example 2.

Then, a supply port having the same shape as shown in Example 1 was attached to the end face of housing at the fluid supply side. A fluid measuring jig having the same shape as shown in Example 1 was provided at the housing end face of the fluid discharge side.

The fiber bundle had packing rate of 55.9% like Example 1 at both end faces before inserting the distribution plate in this configuration. Like Example 1, the both end faces of fiber bundle had packing rate of 69.8% in the central region surrounded by the first salient after inserting the distribution plate while it was 63.9% in the region between the first salient and the second salient and was 58.9% in the other region between the supply port and the second salient.

Next, the inside of column was washed with water to measure the flow distribution of fluid. Table 1 shows the results.

Comparative Example 1

A purification column was prepared by the method shown in Example 1 to measure the flow distribution of fluid, except that the distribution plate was not provided. Table 1 shows the results.

Example 6

PMMA was spun to prepare solid fibers for adsorbent made of PMMA having a fiber diameter of approximately 110 μm (which was determined with V-10A made by Nikon Corporation) according to a well-known method. The solid fibers of 140,000 pieces were bundled to prepare a fiber bundle having surface area of 2.52 $m^2$ to be contained in a cylindrical housing having housing end inner diameter of 55 mm and housing length of 37 mm which was the same as the fiber bundle length, while the fiber bundle end faces had the same position as the housing end faces. In this configuration, the fiber bundle had average packing rate of 57% at end faces.

Next, distribution plates of the same type as shown in FIG. 2 with double ring-shaped salients were provided at both end faces of the fiber bundle. The insertion lengths to the fiber bundle of the first salient at the center and the second salient at the outer periphery side were both 4 mm. The widths of salient tips were 0.1 mm. The first salient had tip diameter of 14.3 mm, inner periphery side diameter of 13.6 mm and outer periphery side diameter of 15.4 mm. The second salient had tip diameter of 35.1 mm, inner periphery side diameter of 35 mm and outer periphery side diameter of 37 mm. The end face of fiber bundle had packing rate of 63% in the central region surrounded by the first salient. It was 59.3% in the region between the first salient and the second salient and was 61.7% in the other region between the supply port and the second salient as well. A mesh filter was bonded onto a surface opposite to the surface forming a salient of the distribution plate supporting body.

Then, a supply port and a discharge port were attached, to both ends of housing at the fluid supply side. Both of the ports having the same shape had a nozzle lower diameter of 4.4 mm. Next, the inside of column was washed with water to seal the supply nozzle and discharge nozzle with a plug to perform a γ-ray irradiation.

The obtained purification column was subjected to a β2-MG clearance measurement (for evaluating adsorptivity) and pressure loss measurement by the following method. Table 2 shows the results.

(2) Measurement Method of β2-MG Clearance

The β2-MG clearance was measured for evaluating a performance of our purification column. It is known that the β2-MG is a causative protein of dialysis-related amyloidosis as a long-term dialysis complication. This measurement was performed as a performance evaluation to determine whether the flow distribution of fluid was controlled to improve the adsorptivity.

First, disodium edetate was added to cow blood to adjust to have hematocrit of 30±3% and total protein of 6.5±0.5 g/dL. The cow blood had been within 5 days after being drawn.

Then, the β2-MG added by 1 mg/L of concentration was stirred in the cow blood. Such prepared cow blood was separated to 2 L for circulation and 5 L for clearance measurement.

Bi circuit inlet was put in a beaker for circulation containing the cow blood of 2 L (at 37° C.) adjusted as described above and then Bi pump was operated at 200 mL/min of flow rate. After draining the liquid discharged from Bo circuit outlet for 90 seconds, the Bo circuit outlet was put in the beaker for circulation to start a circulation.

After having performed the circulation for 1 hour, the pump was stopped.

Then, the Bi circuit inlet was put in the cow blood for clearance measurement while the Bo circuit outlet was put in a beaker for drain.

After the pump was operated for 2 minutes at 200 mL/min, Bi liquid of 10 mL was sampled from cow blood (at 37° C.) for clearance measurement. After the pump was operated 4 minutes and 30 seconds, Bo liquid of 10 mL was sampled from the liquid discharged from the Bo circuit outlet. These samples were stored with freezers at −20° C. or less.

The clearance was calculated by Formula (III) from the concentration of β2-MG of each liquid. Because cow bloods in different lots may have different measured values, cow bloods in the same lot were used in all of Examples and Comparative examples.

$$Co[\mathrm{mL/min}] = (CBi - CBo) \times QB / CBi \qquad (III)$$

In Formula (III), Co indicates β2-MG clearance [mL/min], CBi indicates β2-MG concentration in Bi liquid, CBo indicates β2-MG concentration in Bo liquid and QB indicates flow rate [mL/min] of Bi pump.

(3) Measurement Method of the Pressure Loss

Pressures were measured at the Bi circuit inlet and the Bo circuit outlet just before the sampling process in measurement method (2). The pressure loss of the column was calculated by subtracting the pressure at the Bo circuit outlet from the pressure at the Bi circuit inlet.

Example 7

Solid fibers obtained in the same production lot as Example 6 of 125,000 pieces were bundled to prepare a fiber bundle having surface area of 2.56 $m^2$ to be contained in a cylindrical housing having housing end inner diameter of 55 mm and housing length of 42 mm which was the same as the fiber bundle length, while the fiber bundle end faces had the same position as the housing end faces. The mean filling rate of the thread bunch end face of this verge was 51%.

Next, a distribution plate of the same type as shown in FIG. 5 with 19 pieces of cylindrical salients was provided at the fiber bundle end face of the fluid supply side while only a mesh filter was provided at the fiber bundle end face of the fluid discharge side. All salients had the same shape, which had salient outer periphery diameter of 3 mm and height of 7 mm (which is the same as insertion length in the fiber bundle) while a circular cone shape was formed from the height of approximately 5 mm. The salient outer periphery was provided with equally spaced three salient openings having a shape of slit having width of approximately 1.5 mm from the base part at height of 0 mm to the height at approximately 6 mm.

Among 19 pieces of cylindrical salients, one salient was provided at the center of the distribution plate, equally spaced six salients were provided along a circle having diameter of 22 mm around the center of the distribution plate, equally spaced six salients were provided along another circle having diameter of 38.5 mm as well, and equally spaced six salients were provided along yet another circle having diameter of 44 mm as well. In this configuration, the fiber bundle had average packing rate of 56.6% at end faces.

Near the supporting body outer periphery of the distribution plate, equally spaced thirty circular openings having diameter of 0.5 mm were provided along a circle having diameter of 49 mm around the center of the distribution plate so that the fluid is prevented from stagnation. A mesh filter was bonded onto a surface opposite to the surface forming a salient of the distribution plate supporting body provided at the supply side. The purification column prepared by the same method as Example 6 except for the above-described configuration was subjected to a β2-MG clearance measurement. Table 2 shows the results.

Comparative Example 2

The purification column prepared by the same method as Example 6, except that the distribution plate was not provided while mesh filters having the same specification as

TABLE 1

| Distribution of fluid | Example 1 | Example 2 | Example 3 | Example 4 | Example 5 | Comparative example 1 |
|---|---|---|---|---|---|---|
| Central region | 163% | 113% | 139% | 124% | 122% | 183% |
| Middle region | 100% | 99% | 102% | 101% | 101% | 101% |
| Peripheral region | 94% | 100% | 94% | 97% | 97% | 91% |

* The central region indicates a region surrounded by First salient.
* The middle region indicates a region provided between First salient and Second salient.
* The peripheral region indicates a region provided between Discharge port and Second salient.

Example 1 were provided at both supply side and discharge side. Table 2 shows the results.

According to the results of Examples and Comparative examples, it is understood that excellent adsorptivity and well controlled flow distribution of fluid in our purification column can be achieved by providing a certain distribution plate.

In view of Example 6, it is understood that the packing rate at fiber bundle end face is adjusted and the channel resistance of fluid flowing in the fiber bundle is the greatest in the central region facing the nozzle, so that β2-MG clearance is improved while the uniform velocity distribution of fluid in the fiber bundle is improved like Examples 1 to 5.

In view of Example 7, it is understood that the fluid is distributed from pin-shaped salients provided at each section, so that β2-MG clearance is improved while the uniform velocity distribution of fluid in the fiber bundle is improved.

In view of the results, it seems that the pressure loss is not so different regardless of providing the distribution plate or not. It is understood that, whole fiber bundles have the same level of channel resistance by providing a distribution plate, since the packing rate at fiber bundle end increases to increase channel resistance while uneven flow of fluid is improved to decrease the channel resistance inside the fiber bundle.

INDUSTRIAL APPLICATIONS OF THE INVENTION

Our purification column can be used as water treatment, refinement, blood purification or the like.

EXPLANATION OF SYMBOLS

100: purification column
101: housing
102: supply port
103: discharge port
104: supply nozzle
105: discharge nozzle
106: joint
200: adsorbent
201: adsorbent end face
300: distribution plate
301: supporting body
302: opening
303: salient
303a: salient
303b: salient
304: salient inner periphery
305: salient tip
306: salient outer periphery

TABLE 2

| | Inside Diameter of housing edge [mm] | Fiber bundle length [mm] | Membrane surface area [m²] | Distribution plate | Length of inserted salient [mm] | Packing rate of fiber bundle edge [%] | β2-MG clearance [mm/min] | Pressure loss [kPa] |
|---|---|---|---|---|---|---|---|---|
| Example 6 | 55 | 37 | 2.52 | Provided at both sides | 4 | 63.0 | 44.5 | 3.5 |
| Example 7 | 55 | 42 | 2.56 | Provided at supply side only | 7 | 56.6 | 46.3 | 5.9 |
| Comparative example 2 | 55 | 37 | 2.52 | None | — | 57.0 | 41.2 | 4.5 |

* The packing rate of fiber bundle edge in Example 6 has been determined at the center of distribution plate.
* The packing rate of fiber bundle edge in Example 7 has been determined at the supply side of the distribution plate provided.

307: salient opening
400: filter
401: filter supporting body
500: purification column
Aa1: adsorbent cross-section area at adsorbent end face surrounded by salient 303a
Aa2: adsorbent cross-section area between salients 303b and 303a
Aa3: adsorbent cross-section area between supply port 102 and salient 303b
Ab1: adsorbent cross-section area of salient 303a at adsorbent end face 201
Ab2: adsorbent cross-section area of salient 303b at adsorbent end face 201

The invention claimed is:

1. A purification column comprising:
an adsorbent;
a case which contains the adsorbent and has a cylindrical housing, a supply port for a fluid at one end of the housing and a discharge port for the fluid at another end of the housing; and
a distribution plate provided at an end face side of the adsorbent,
the distribution plate having:
a plurality of openings capable of communicating the fluid;
a supporting body; and
at least one salient extending from the supporting body toward the adsorbent,
the at least one salient being inserted at least partially into the adsorbent, wherein the adsorbent has an increased packing rate at an adsorbent end face relative to an adsorbent packing rate away from the adsorbent end face due to the insertion of the at least one salient into the adsorbent.

2. The purification column according to claim 1, wherein the adsorbent is formed into a fiber bundle consisting of a plurality of fibers.

3. The purification column according to claim 1, wherein the adsorbent is formed into a plurality of beads.

4. The purification column according to claim 1, wherein the adsorbent has an increased packing rate at an adsorbent end face relative to a packing rate away from the adsorbent end face of 40% to 80%, due to the insertion of the at least one salient into the adsorbent, wherein the increased packing rate is defined by Formula I:

Increased packing rate at an adsorbent end face[%]= (Cross-section area of adsorbent at end face+ Cross-section area of salient at end face of adsorbent)/(Inner cross-section area of case at end face of adsorbent)×100[%]   [Formula I].

5. The purification column according to claim 1, wherein the at least one salient is formed into a circular ring around the central axis of the housing.

6. The purification column according to claim 1, comprising a plurality of salients, wherein each of the salients is formed into a circular ring around the central axis of the housing.

7. The purification column according to claim 5, wherein at least one of an inner periphery and an outer periphery of the at least one salient formed into the circular ring has an inclination to be tapered from the supporting body toward a tip of the at least one salient.

8. The purification column according to claim 6, wherein at least one of an inner periphery and an outer periphery of each of the salients formed into the circular ring has an inclination to be tapered from the supporting body toward a tip of each salient.

* * * * *